(12) United States Patent
Schaub

(10) Patent No.: US 11,826,286 B2
(45) Date of Patent: Nov. 28, 2023

(54) APPARATUS SUPPORT, IN PARTICULAR FOR FASTENING A MOBILE MEDICAL APPARATUS, AND MEDICAL ASSEMBLY HAVING SAME

(71) Applicant: Markus Schaub, Wetzlar (DE)

(72) Inventor: Markus Schaub, Wetzlar (DE)

(*) Notice: Subject to any disclaimer, the term of this patent is extended or adjusted under 35 U.S.C. 154(b) by 0 days.

(21) Appl. No.: 17/386,614

(22) Filed: Jul. 28, 2021

(65) Prior Publication Data

US 2022/0031543 A1 Feb. 3, 2022

(30) Foreign Application Priority Data

Jul. 28, 2020 (DE) .................. 10 2020 119 909.0

(51) Int. Cl.
*F16M 11/22* (2006.01)
*A61G 12/00* (2006.01)
*F16M 13/02* (2006.01)

(52) U.S. Cl.
CPC ........... *A61G 12/005* (2013.01); *F16M 13/02* (2013.01)

(58) Field of Classification Search
CPC .. A61G 12/005; A61G 7/0503; A61G 13/107; A61G 3/001; F16M 13/02; F16M 11/22; F16M 13/022; F16M 11/041; A61M 5/1414; F16F 15/08
See application file for complete search history.

(56) References Cited

U.S. PATENT DOCUMENTS

| 2012/0068040 A1 | 3/2012 | Venghaus | |
| 2017/0150812 A1* | 6/2017 | Tomomatsu | ............ H04M 1/04 |
| 2022/0034444 A1* | 2/2022 | Bouchard | ................. F16B 2/10 |

FOREIGN PATENT DOCUMENTS

| CN | 201 814 746 | 5/2011 | |
| CN | 210 510 956 | 5/2020 | |
| DE | 10 2008 039651 | 2/2010 | |
| DE | 10 2012 025 066 | 6/2013 | |
| DE | 202015105917 U1 * | 2/2016 | ............... A45F 3/08 |
| DE | 10 2017 104 754 | 9/2018 | |
| JP | 01-133916 | 9/1989 | |
| WO | 2016/106727 | 7/2016 | |

* cited by examiner

*Primary Examiner* — Terrell L McKinnon
*Assistant Examiner* — Jerry Nmn Olivier
(74) *Attorney, Agent, or Firm* — Clark & Brody LP

(57) ABSTRACT

An apparatus support, intended for fastening a mobile medical apparatus such as a defibrillator, an oxygen apparatus, a ventilator, a monitor, an infusion apparatus, an inhalation apparatus, an electrocardiograph, a transfusion pump, a life support system, an extracorporeal system, and a heart-lung machine, has a wall holder and a mounting plate. In the intended mounting state, the apparatus is oriented at least substantially or exactly horizontally and has upper and lower faces and side edges. The mounting plate has a fastening device for fastening a medical apparatus that is to be arranged on the upper face, and a damping device via which the mounting plate is fixed on the wall holder. The invention further relates to a medical assembly having such an apparatus support and having a medical apparatus as described above.

10 Claims, 4 Drawing Sheets

APPARATUS SUPPORT, IN PARTICULAR FOR FASTENING A MOBILE MEDICAL APPARATUS, AND MEDICAL ASSEMBLY HAVING SAME

The invention relates to an apparatus support, in particular for fastening a mobile medical apparatus from the group comprising a defibrillator, an oxygen apparatus, a ventilator, a monitor, an infusion apparatus, an inhalation apparatus, an electrocardiograph, a transfusion pump, a life support system, an extracorporeal system, and a heart-lung machine (HLM.

In situations where patients are being treated in vehicles, medical apparatuses have to be made secure in order to be able to provide reliable care without representing a source of danger. For this purpose, apparatus supports are used which, for example, serve to fasten defibrillators, ventilators, monitors, infusion apparatuses, inhalers/inhalation apparatuses, electrocardiographs and transfusion pumps.

Thus, DE 10 2017 104 754 A1 discloses an apparatus support which is used to fasten a mobile oxygen apparatus or ventilator for mobile intensive care and which can be fixed on a vertically oriented carrier element. It has a mobile unit and a fastening unit. The mobile unit has a receiving body which forms a receiving space for an oxygen apparatus or ventilator. It comprises a horizontally oriented mounting plate which, on the upper face, has positioning pins and lateral upturns. The apparatus thus received cannot therefore slip sideways. The mobile unit has a first suspension element and a first locking element, which are each arranged on a rear face of the receiving body, wherein the first locking element is arranged higher than the first suspension element. The fastening unit has a mounting plate on which there are arranged a second suspension element for the suspension of the first suspension element, and a second locking element for locked connection to the first locking element.

A disadvantage of this support is that it is highly specific to mobile oxygen apparatuses or ventilators. Moreover, vibrations can lead to incorrect apparatus functions and can also permanently damage the medical apparatus.

The object of the invention is therefore to make available an apparatus support which offers a high degree of variability in terms of the apparatus used and which allows the apparatus to operate reliably and free from damage. The technical solution should be as convenient as possible and economical.

The invention relates to an apparatus support, in particular for fastening a mobile medical apparatus from the group comprising a defibrillator, an oxygen apparatus, a ventilator, a monitor, an infusion apparatus, an inhalation apparatus, an electrocardiograph, a transfusion pump, a life support system, an extracorporeal system, and a heart-lung machine (HLM), having a wall holder, and having a mounting plate which, in the intended mounting state, is oriented at least substantially or exactly horizontally and has an upper face, a lower face and side edges. The mounting plate has, on the upper face, a fastening device for fastening a medical apparatus that is to be arranged on the upper face. The apparatus support also has a damping device via which the mounting plate is fixed on the wall holder.

The advantage of this is that medical apparatuses that are arranged on the mounting plate are damped with respect to the wall holder and thus with respect to a fastening location such as a wall of an ambulance, helicopter, airplane or rescue boat. In this way, the safe operation of the medical apparatus is improved, and damage is avoided. For this purpose, the damping device should have a damping property which, in the intended mounting state, acts vertically. Since most medical apparatuses are in any case already designed to stand on a level supporting surface, the horizontally oriented mounting plate is expedient for ensuring that the medical apparatus is fastened with the least possible effort.

According to a particular embodiment, the damping device is arranged between a carrier element of the wall holder and the mounting plate, wherein the carrier element, in the intended mounting state, is oriented at least substantially or exactly horizontally. In this way, a stiff support is obtained, and the damping device can be arranged away from the flexurally loaded zone between mounting plate and wall holder. The orientation is to be understood relative to the fastening object. If the fastening object moves, for example a boat, airplane or land vehicle, this can lead to a geodetic position change on account of the locomotion and vehicle position.

Optionally, the carrier element can have a carrier plate which is arranged at a distance under the mounting plate. In the intended mounting state, the carrier plate can in particular be oriented exactly or at least substantially parallel to the mounting plate. This results in a stable substructure beneath the mounting plate. Moreover, when the apparatus support is set down on a surface, the medical apparatus is protected by the damping device against impacts and vibrations. On the lower face of the carrier plate, supporting feet and/or fixing elements can optionally be arranged for airline rails or cargo rails. With supporting feet, a secure stand would be ensured, and the carrier plate would not be damaged and would be kept a distance above a wet ground surface. The optional fixing elements serve for reliable and rapid fixing to the airline rails or cargo rails. The latter preferably have a T-shaped groove, in the groove opening of which insertion holes, in particular circular insertion holes, are formed at defined spacings. On the apparatus support, the optional fixing elements provided for this purpose preferably have fastening heads, optionally also juxtaposed rows thereof. These fastening heads can be plugged into the insertion holes and are then able to move in the airline rail or cargo rail. As soon as the fastening heads and insertion holes are no longer aligned, securing orthogonal to the rail is produced. The position along the airline rail or cargo rail is preferably secured by a mechanically releasable latch element, in particular with a round bolt. A latch element of this kind is preferably mounted on the carrier plate, preferably with spring loading. For the actuation, a variant is expedient that has a latch lever, with which the latch element can be moved to an open position. For the latch lever and the latch element, it is possible, for example, for a latch housing to be arranged on the upper face of the carrier plate.

The mounting plate is preferably supported in a floating fashion on the wall holder via the damping device. Horizontally acting impacts and vibrations are accordingly damped.

Specifically, the damping device can have between one and twelve damping elements, preferably between three and six damping elements, and particularly preferably exactly four damping elements, on the lower face of the mounting plate. Although one damping element can suffice, better damping of tumbling movements and rotational oscillations in particular can be achieved by using a plurality of damping elements. With distribution of the damping elements, the total weight of the damping elements overall also decreases. When the mounting plate has a rectangular basic shape, it proves particularly advantageous to provide exactly four damping elements, i.e. one for each corner of the rectangular basic shape. This results in a stable support with low weight.

There is the possibility that the one or more damping elements are each arranged on a carrier top of the wall holder, wherein the carrier top, in the intended mounting state, is oriented at least substantially or exactly horizontally. The mounting plate thus stands as it were on the damping elements, which in turn sit on the carrier top.

In one embodiment, the one or more damping elements are each formed by a rubber buffer. Such rubber buffers are economical and function safely and hygienically over a long period of time. The rubber buffer preferably has a rubber layer between two connecting elements. The rubber layer can be vulcanized on, for example, between two plates, for example metal plates. The connecting elements can have screw bolts, which are fixed in particular on the metal plates. Optionally, the connecting elements can be connected to one another via a mechanical securing coupling, which takes effect if the rubber layer is damaged or overloaded.

Optionally, the mounting plate can be secured with movement play on the wall holder via a mechanical securing coupling, wherein the securing coupling secures the mounting plate on the wall holder if the damping device is overloaded or fails. Accordingly, the medical apparatus cannot come falling down if the damping device fails. Moreover, the damping device is protected against overloads if a mechanical stop prevents these. The mechanical securing coupling can be formed away from the damping device or else is part of the damping device or of the damping elements.

In a particular embodiment, the wall holder has a vertical holding limb, on the front face of which the mounting plate is arranged, and on the opposite rear face of which holding elements are arranged for the wall fastening. The vertical holding limb ensures good dissipation of force into a wall without any substantial bending moments.

The wall holder preferably has a holding frame, which forms the vertical holding limb. A frame is composed of struts, as a result of which a low weight is achieved along with a high degree of stiffness. The carrier plate can be fastened to the holding frame. For this purpose, the holding frame preferably has two L limbs arranged spaced apart and adjacent and, in the intended mounting state, vertically oriented limbs of these L limbs form the vertical holding limb of the wall holder. In the intended mounting state, horizontally oriented limbs of these L limbs can then be arranged at a distance under the mounting plate.

Furthermore, the holding elements can have suspension hooks. In this way, the wall holder can be suspended quickly on a fastening rail or the like. The suspension hooks are preferably arranged at two height lines, in particular in order to suspend the apparatus support on two fastening rails that are oriented in parallel. This results in a stable connection that is secured against tilting. Optionally, the holding elements have latch elements and/or quick-release clamps, in particular in order to permit rapid assembly on a fastening rail, for example on a wall. Latch elements are particularly convenient but offer a hold that is only partially free of play. Quick-release couplings permit a firm connection that is free of play, and they can be released in sequence and facilitate disassembly.

Moreover, the holding elements can have pivoting hooks which, for suspension on a horizontally oriented element, are mounted pivotably about an axis which, in the intended mounting state, is oriented exactly or at least substantially vertically. With the aid of these, the apparatus support can also be suspended on fastening sites that are not intended for this purpose. By virtue of the pivoting movement, they can also be brought from the use position to a stowage position, in which they do not get in the way, in particular in which they do not collide with a mounting wall. To secure the pivoting hooks in the stowage position, an embodiment is expedient in which the pivoting hooks are secured in this stowage position by a spring pressure piece. To prevent damage to paint on the part on which the pivoting hooks are suspended, it is expedient for the pivoting hooks to be coated, for example with a rubber coating. A typical case of use for the suspension with the pivoting hooks is that of gurneys without a fastening rail.

In a particular embodiment, the fastening device has, on the upper face of the mounting plate, a receiving contour for receiving, with form-fit engagement, an underside of a medical apparatus that is to be received. With such form-fit engagement, stable fastening can be quickly obtained in a defined position. The underside of the apparatus can be formed by a housing or by a tubular frame. The receiving contour can have a curved groove. The latter prevents sliding movements and also rotational movements if a negative of the same shape, in particular a rib or a tube of the medical apparatus, is introduced therein.

Moreover, the fastening device can have, on the upper face of the mounting plate, securing elements by which a medical apparatus that is to be received is fixed with form-fit engagement. Optionally, the securing elements are of a self-securing design, for which purpose they are preferably mounted pivotably about a vertical pivot axis and are secured by latching. In this way, the securing elements can pivot into an opening, over a base plate or over a tube of a tubular framework of the medical apparatus. Specifically, the securing elements can be pivotable latch levers. The securing elements preferably have latch positions, for example with a spring pressure piece (for example also a spring-mounted ball) which is pressed into latch recesses. It may be particularly helpful to secure the securing elements in an open position, such that the medical apparatus can be inserted and easily removed. It is also helpful to secure the securing elements in a closed position, such that the medical apparatus is well secured. To protect a coating of the medical apparatus, it is expedient to coat the securing elements at the contact faces or to provide sliding pieces there, for example made of polyamide.

In one embodiment variant, the mounting plate has a web structure on its lower face, wherein hollows are formed in the interspaces of the web structure. In this way, the mounting plate is stiff and at the same time very light.

Optionally, the carrier plate has a web structure on its lower face, wherein hollows are formed in the interspaces of the web structure. In this way, the carrier plate is stiff and at the same time very light.

For reasons of lightweight construction, a design is expedient in which the mounting plate has at least one plate hole, wherein the one or more plate holes make up at least 15% of the surface area of the upper face of the mounting plate.

Similarly, for reasons of lightweight construction, a design is expedient in which the carrier plate has at least one plate hole, wherein the plate holes make up at least 10% of the surface area of the upper face of the carrier plate.

In a particular embodiment, the mounting plate and the carrier plate each have a plate hole, which plate holes are arranged in vertical alignment. This makes it possible to have blood, blood plasma or other preserved substances from the medical apparatus above the mounting plate hang down through the mounting plate and the carrier plate. For this purpose, the aligned plate holes are preferably at least 6 cm wide and at least 8 cm long. The basic shape of these holes can be, inter alia, rectangular, round or oval.

In addition, the apparatus support can have an infusion stand which, in the intended mounting state, is oriented exactly or at least substantially vertically. In this way, the medical apparatus and/or the patient can be supplied directly with a medicament or similar. During transport, it suffices to transport the whole apparatus support, as a result of which fewer personnel are needed. Preferably, the infusion stand has a suspension hook in the region of the upper end.

This suspension hook serves for suspending a bottle or a bag. In the intended mounting state, the infusion stand preferably forms the highest point of the apparatus support. The infusion stand is preferably fixed on the wall holder. In this way, the mast-like bending forces do not act on the damped mounting plate. The infusion stand is preferably telescopically extensible. In this way, it can be temporarily pushed together when not needed, or during transport, and takes up less space. In the region of the telescopic connection between two standard tube sections, it is expedient to provide a sleeve protruding between the tubes. This limits the frictional contact to the region of the sleeve and, with a suitable choice of material, can avoid noise development. A sleeve made of plastic is suitable, for example. For secure locking, it is expedient to insert, between two standard tube sections mounted telescopically on each other, a push-button element or a spring metal piece, which engages resiliently in latch holes.

The carrier plate, the mounting plate, the holding frame and the infusion stand can advantageously be made of a lightweight construction material, in particular of aluminum or a polymer composition or a combination of these.

The invention further relates to medical assembly having an apparatus support as described above and below and having a mobile medical apparatus from the group comprising a defibrillator, an oxygen apparatus, a ventilator, a monitor, an infusion apparatus, an inhalation apparatus, an electrocardiograph, a transfusion pump, a life support system, an extracorporeal system, and a heart-lung machine (HLM), wherein the mobile medical apparatus has a housing underside or a tubular frame, with which the mobile medical apparatus is arranged on the upper face of the mounting plate and is fastened with the fastening device.

Further features, details and advantages of the invention will become clear from the wording of the claims and from the following description of illustrative embodiments made with reference to the drawings, in which:

Figure 1:
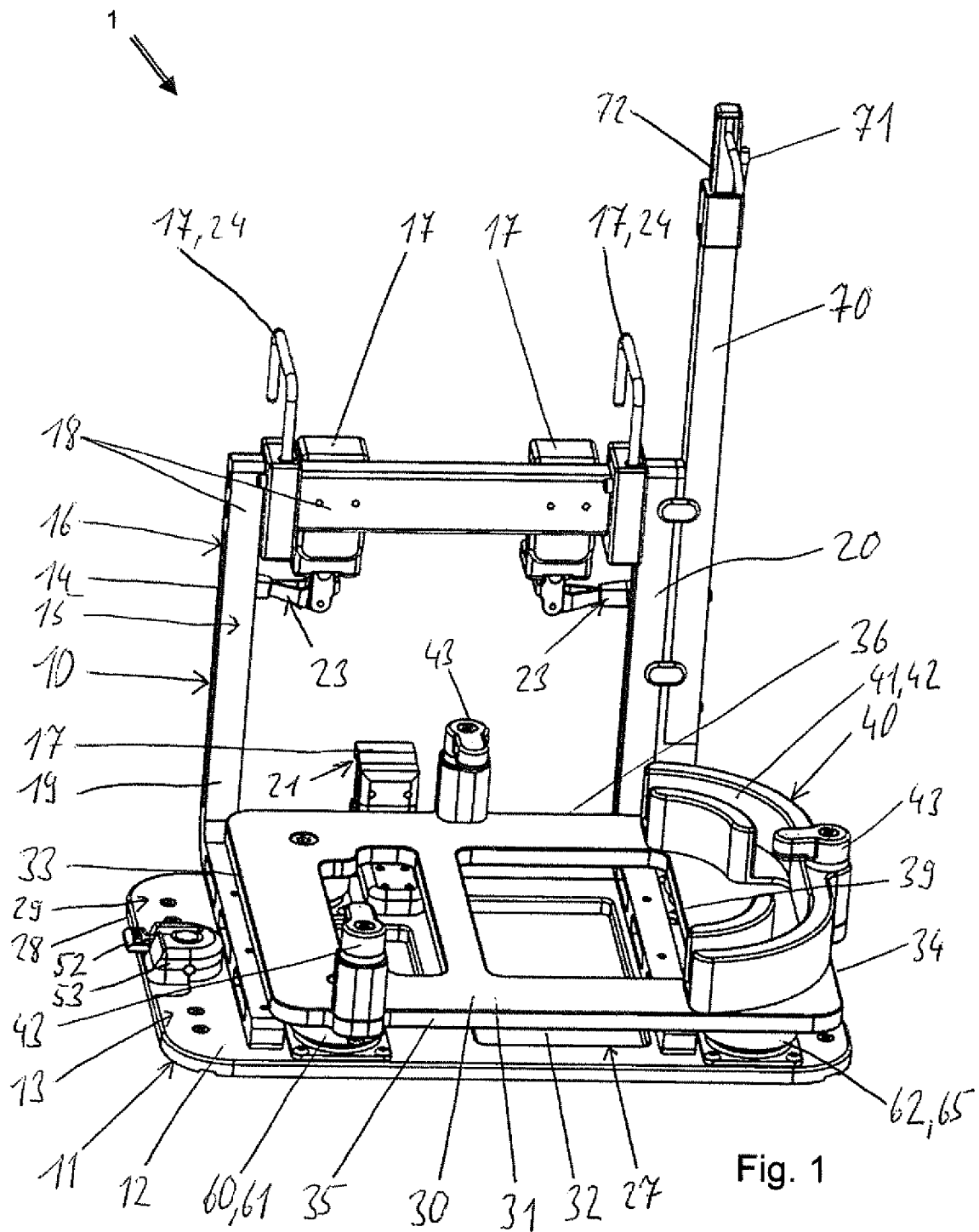
FIG. 1 shows a perspective view of an apparatus support from the front and obliquely from above.
Figure 2:
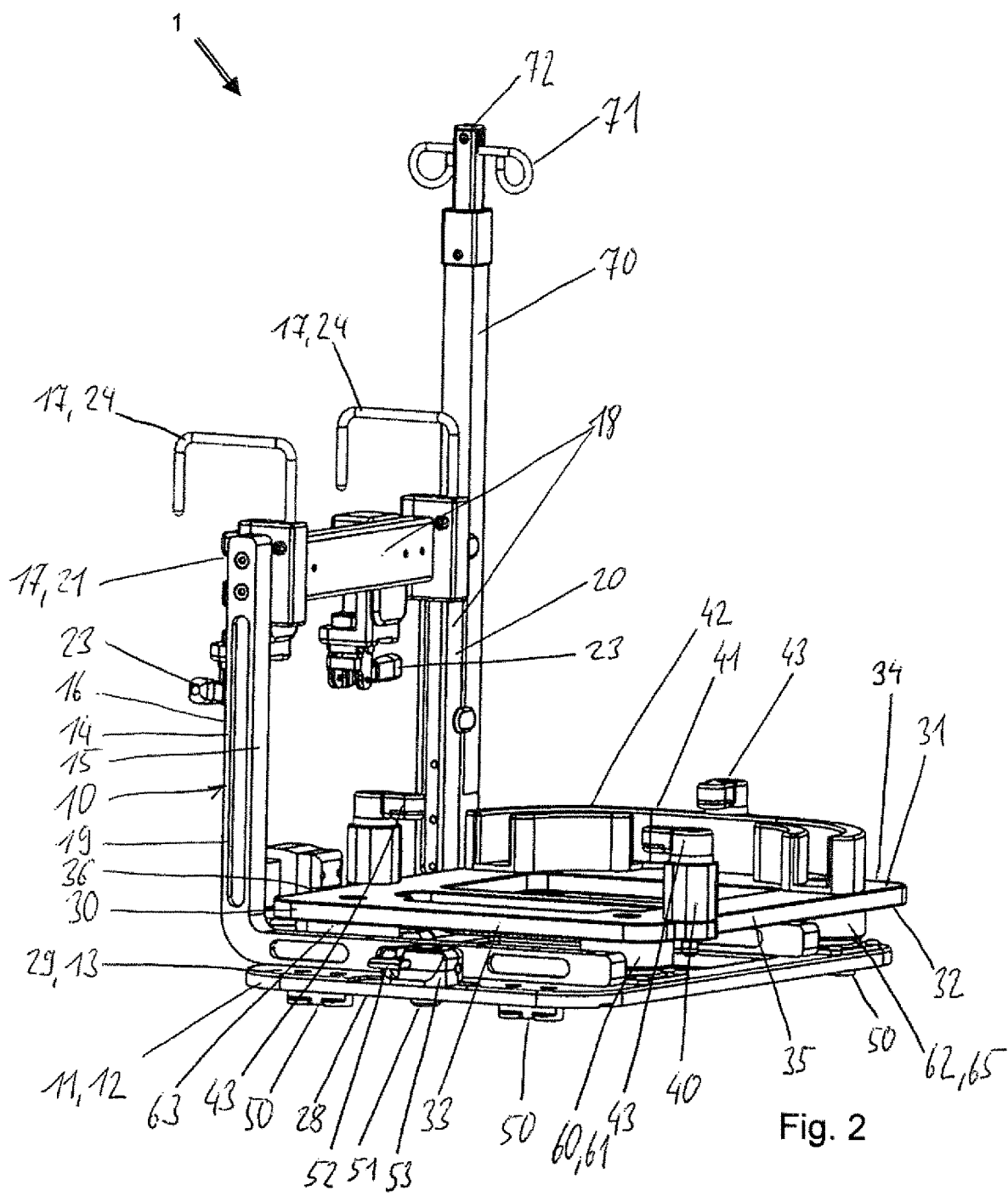
FIG. 2 shows a perspective view of the apparatus support according to FIG. 1 from the side.
Figure 3:
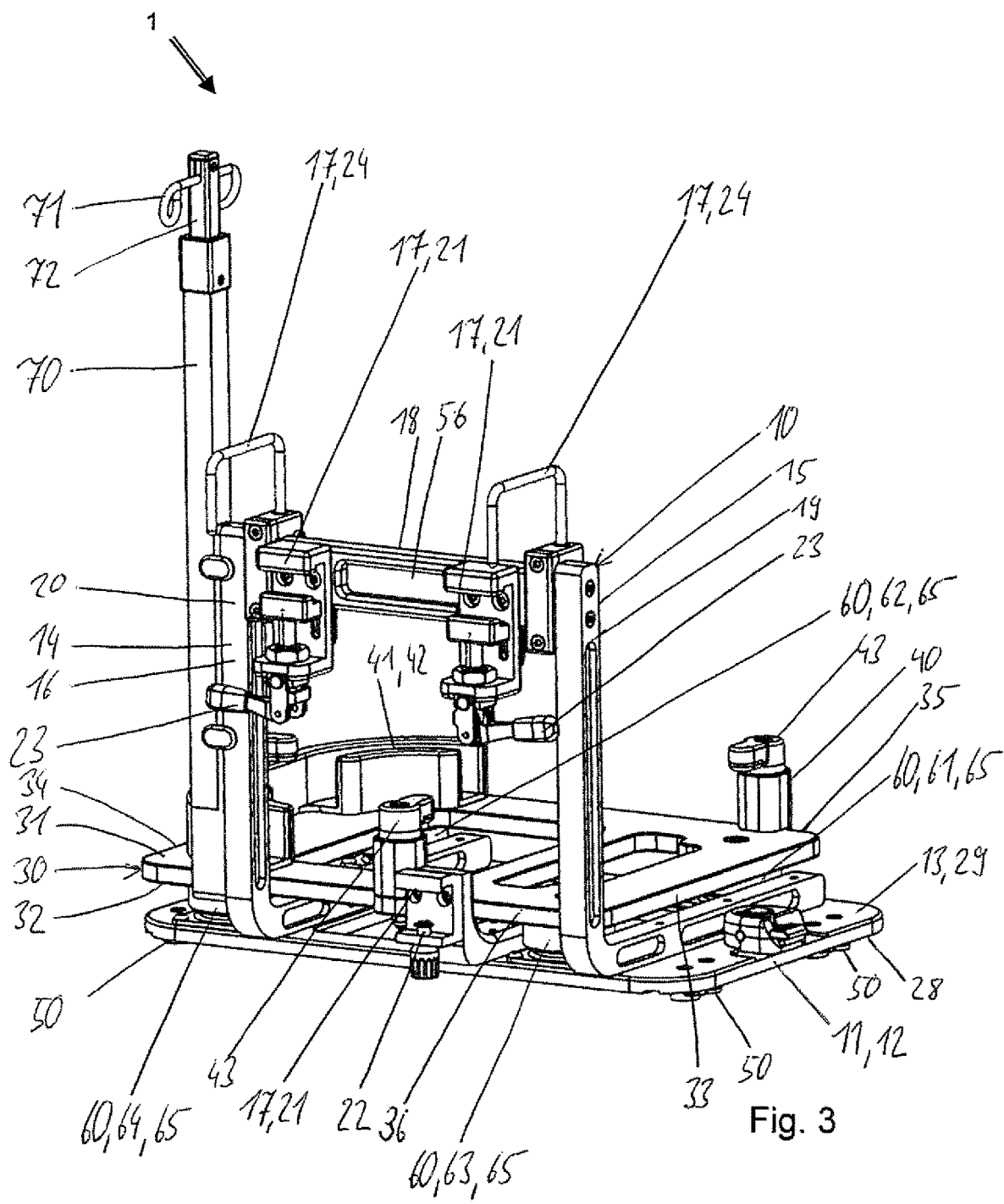
FIG. 3 shows a perspective view of the apparatus support according to FIG. 1 from the rear and obliquely from above.
Figure 4:
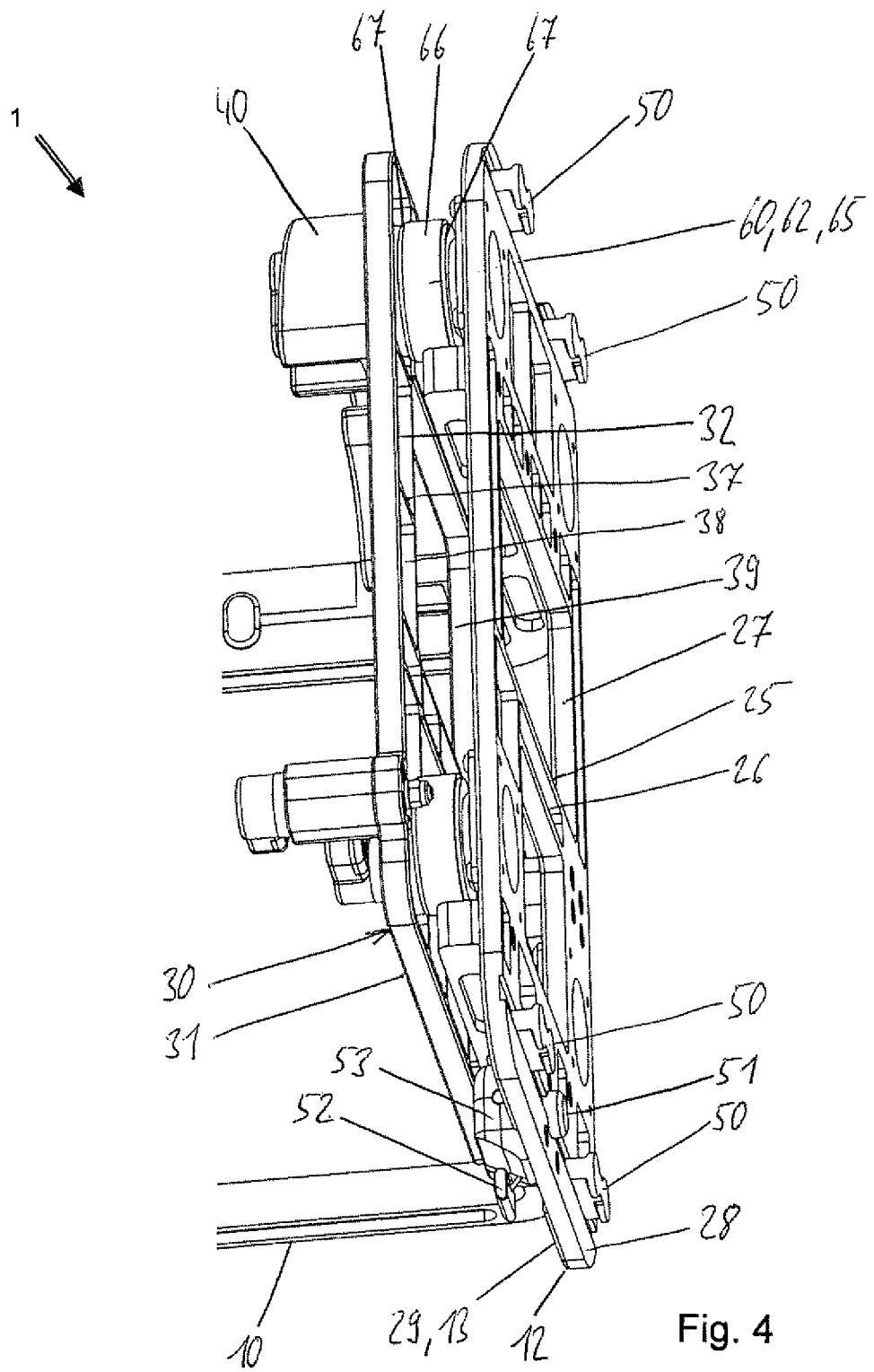
FIG. 4 shows a perspective partial view of the apparatus support according to FIG. 1 from below.

FIGS. 1, 2, 3 and 4 each show the same apparatus support 1 from different perspectives, with FIG. 4 showing only a partial view. The same reference numbers thus correspond to the same components, and the figures are described jointly.

The apparatus support 1 according to FIGS. 1, 2, 3 and 4 serves for fastening a mobile medical apparatus from the group comprising a defibrillator, an oxygen apparatus, a ventilator, a monitor, an infusion apparatus, an inhalation apparatus, an electrocardiograph, a transfusion pump, a life support system, an extracorporeal system, and a heart-lung machine (HLM). It has a wall holder 10 and a mounting plate 30.

In the intended mounting state, the mounting plate 30 is oriented at least substantially or exactly horizontally and has an upper face 31, a lower face 32 and side edges 33, 34, 35, 36. On the upper face 31, the mounting plate 30 has a fastening device 40 for fastening a medical apparatus that is to be arranged on the upper face 31.

Furthermore, the apparatus support 1 has a damping device 60 via which the mounting plate 30 is fixed on the wall holder 10. The damping device 60 is arranged between a carrier element 11, in particular a carrier plate 12, of the wall holder 10 and of the mounting plate 30. In the intended mounting state, the carrier element 11, namely the carrier plate 12, is oriented at least substantially or exactly horizontally, whereby it is arranged at a distance under the mounting plate 30 and is oriented parallel to the latter.

As will be seen in particular from FIG. 4, fixing elements 50 for airline rails or cargo rails are arranged on the lower face 28 of the carrier plate 12. The fixing elements 50 are designed to be exchangeable and serve for reliable and rapid fixing on the airline rails or cargo rails. The latter preferably have a T-shaped groove, in the groove opening of which insertion holes, in particular circular insertion holes, are formed at defined spacings. On the apparatus support, the fixing elements 50 provided for this purpose preferably have fastening heads, which are in part juxtaposed, particularly in each case in pairs. These fastening heads can be plugged into the insertion holes and are then able to move in the airline rail or cargo rail. As soon as the fastening heads and insertion holes are no longer aligned, securing orthogonal to the rail is produced. The position along the airline rail or cargo rail is secured by a mechanically releasable latch element 51, in particular with a round bolt. This latch element is mounted on the carrier plate 12, preferably with spring loading, and, depending on the position, protrudes by a different distance below the lower face 28 of the carrier plate 12. For the actuation of the latch element 51, a latch lever 52 is provided, with which the latch element 51 can be moved to an open position. The latch lever 52 and the latch element 51 are mounted in a latch housing 53, which is arranged on the upper face 29 of the carrier plate 12.

It will also be seen from FIG. 4 that the carrier plate 12 has, on the lower face 28, a web structure 25, such that hollows 26 are formed in the interspaces of the web structure 25. To save weight, two plate holes 27 are also formed in the carrier plate 12, which plate holes 27 make up at least 10% of the surface area of the upper face 29 of the carrier plate 12.

The wall holder 10 forms a vertical holding limb 14, on the front face 15 of which the mounting plate 30 is arranged, and on the opposite rear face 16 of which holding elements 17 are arranged for the wall fastening. A wall is understood to mean all vertically oriented structural elements that can serve as a fastening base. Fastening rails are preferably arranged on this wall.

Part of the wall holder 10 is a holding frame 18 which forms the vertical holding limb 14. The holding frame 18 has two L limbs 19, 20 which are arranged spaced apart and adjacent and which are connected to each other via crosspieces. In the intended mounting state, a vertically oriented limb of these L limbs 19, 20 forms the vertical holding limb 14 of the wall holder 10 or part thereof. In the intended mounting state, horizontally oriented limbs of the L limbs 19, 20 are however arranged, at a distance under the mounting plate 30, on the carrier plate 10.

The holding elements 17 on the rear face 16 of the vertical holding limb 14 have suspension hooks 21 (see in particular FIG. 3). The three suspension hooks 21 are arranged on two height lines, in order to suspend the apparatus support 1 on two parallel fastening rails. The lower of the holding elements 17 has a latch element 22, and the two upper holding elements 17 each have a quick-release clamp 23.

As additional holding elements 17, pivoting hooks 24 are provided which, for suspension on a horizontally oriented element, are mounted pivotably about an axis which, in the intended mounting state, is oriented exactly or at least substantially vertically. If the pivoting hooks 24 are not needed, they are rotated such that they point toward each other. They are each held in this stowage position by a respective spring pressure piece 55.

For simplified handling, a hollow 56 is formed in the upper crosspiece of the holding frame 18. This hollow 56 serves in particular to reduce weight but in the present case can also provide an improved grip for carrying.

The carrier plate 12, now fastened to the lower face of the L-limbs 19, 20, hangs on the holding frame 18. The mounting plate 30 is mounted in a floating fashion on the wall holder 10 via the damping device 60. For this purpose, the damping device 60 has precisely four damping elements 61, 62, 63, 64 between the lower face 31 of the mounting plate 30 and the upper face 29 of the carrier plate 12. The carrier plate 12 has a rectangular basic shape, and in each case one of the damping elements 61, 62, 63, 64 sits in the region of one of the corners of the rectangular basic shape.

As is indicated in particular in FIG. 4, the damping elements 61, 62, 63, 64 are each formed by a rubber buffer 65, which has a rubber insert layer 66 between two connecting elements 67. One of the two connecting elements 67 is fixed on the carrier plate 12 and one on the mounting plate 30.

Optionally, the mounting plate 30 can be secured with movement play on the wall holder 10 via a mechanical securing coupling, wherein the securing coupling secures the mounting plate 30 on the wall holder if the damping device 60 is overloaded or fails. The securing coupling can also be formed in the core of the rubber insert layer 66, a mechanical connection being formed there with play between the connecting elements 67.

The fastening device 40 on the upper face 31 of the mounting plate 30 has a receiving contour 41 in the form of a curved groove 42 for receiving, with form-fit engagement, an apparatus underside or tubular frame of a medical apparatus that is to be received. The fastening device 40 on the upper face 31 of the mounting plate 30 additionally has securing elements 43, in particular latch levers, by which a medical apparatus that is to be received is fixed with form-fit engagement. The securing elements 43 are of a self-securing design, for which purpose they are mounted pivotably about a vertical pivot axis. Latch positions are provided for holding the securing elements 43 in an opened position and a closed position. For this purpose, a spring pressure piece is in each case arranged between the securing element 43 and a substructure and, in different rotational angle positions of the securing element 43, engages in opposite latch depressions.

The mounting plate 30 also has a web structure 37 on the lower face 32, wherein hollows 38 are formed in the interspaces of the web structure 37. In addition, two plate holes 39 are formed in the mounting plate 30 and make up at least 15% of the surface area of the upper face 31 of the mounting plate 30. One of the two plate holes 39 of the mounting plate 30 is in alignment with one of the two plate holes 27 of the carrier plate 12, such that a bag containing a preserved substance can hang down through the mounting plate 30 and the carrier plate 12.

Extending parallel to the vertical holding limb 14 is an infusion stand 70, which is connected to the vertical holding limb 14 and, in the intended mounting state, is oriented exactly or at least substantially vertically. In the intended mounting state, the infusion stand 70 forms the highest point of the apparatus support 1.

The infusion stand 70 is of a telescopic design with an extensible telescope tube 72. A suspension hook 71 is formed at the upper end of the infusion stand 70. In the region in which the telescope tube is mounted displaceably in an outer tube 73, a sleeve 74 made of plastic sits between the two telescopic tubes 72, 73 and thus forms a slide bearing. The telescope tube 72 has a spring metal piece 75 which is designed for engaging in latching holes of the outer tube 73. The outer tube 73 is rigidly connected to the holding frame 18. Optionally, an outer tube of the infusion stand 70 can also be designed in one piece with the holding frame 18.

The invention is not limited to one of the embodiments described above and can instead be modified in a variety of ways.

All of the features and advantages that emerge from the claims, from the description and from the drawing, including structural details, spatial arrangements and method steps, may be essential to the invention both individually and in a wide variety of combinations.

| List of reference signs | |
|---|---|
| 1 | apparatus support |
| 10 | wall holder |
| 11 | carrier element |
| 12 | carrier plate |
| 13 | carrier top |
| 14 | vertical holding limb |
| 15 | front face (vertical holding limb) |
| 16 | rear face (vertical holding limb) |
| 17 | holding elements for wall fastening |
| 18 | holding frame |
| 19 | L limb |
| 20 | L limb |
| 21 | suspension hook |
| 22 | latch element |
| 23 | quick-release clamp |
| 24 | pivoting hook |
| 25 | web structure |
| 26 | hollow |
| 27 | plate hole (carrier plate) |
| 28 | lower face (carrier plate) |
| 29 | upper face (carrier plate) |
| 30 | mounting plate |
| 31 | upper face |
| 32 | lower face |
| 33 | side edge |
| 34 | side edge |
| 35 | side edge |
| 36 | side edge |
| 37 | web structure |
| 38 | hollow |
| 39 | plate hole |
| 40 | fastening device |
| 41 | receiving contour |
| 42 | curved groove |
| 43 | securing element |
| 50 | securing element |
| 51 | latch element |
| 52 | latch lever |
| 53 | latch housing |
| 55 | spring pressure piece (pivoting hook) |
| 56 | hollow (wall holder) |
| 60 | damping device |
| 61 | damping element |
| 62 | damping element |
| 63 | damping element |
| 64 | damping element |

| List of reference signs | |
|---|---|
| 65 | rubber buffer |
| 66 | rubber insert layer |
| 67 | connecting elements |
| 70 | infusion stand |
| 71 | suspension hook |
| 72 | telescope tube |
| 73 | outer tube |
| 74 | sleeve |
| 75 | spring metal piece |

The invention claimed is:

1. An apparatus support (1), in particular for fastening a mobile medical apparatus from the group comprising a defibrillator, an oxygen apparatus, a ventilator, a monitor, an infusion apparatus, an inhalation apparatus, an electrocardiograph, a transfusion pump, a life support system, an extracorporeal system, and a heart-lung machine (HLM),
having a wall holder (10), and
having a mounting plate (30)
which, in the intended mounting state, is oriented at least substantially or exactly horizontally and has an upper face (31), a lower face (32) and side edges (33, 34, 35, 36),
wherein the mounting plate (30) has, on the upper face (31), a fastening device (40) for fastening a medical apparatus that is to be arranged on the upper face (31),
characterized in that
the apparatus support (1) has a damping device (60) via which the mounting plate (30) is fixed on the wall holder (10) and the wall holder (10) has a vertical holding limb (14), the vertical holding limb (14) having a front face (15) and an opposite rear face (16), the mounting plate (30) arranged on the front face (15), and holding elements (17) arranged on the rear face (16) for fastening the apparatus support to a wall.

2. The apparatus support (1) as claimed in claim 1, characterized in that the damping device (60) is arranged between a carrier element (11) of the wall holder (10) and the mounting plate (30), wherein the carrier element (11), in the intended mounting state, is oriented at least substantially or exactly horizontally.

3. The apparatus support (1) as claimed in claim 1, characterized in that the carrier element (11) has a carrier plate (12) which is arranged at a distance under the mounting plate (30).

4. The apparatus support (1) as claimed in claim 1, characterized in that the damping device (60) has between one and twelve damping elements (61, 62, 63, 64) on the lower face (31) of the mounting plate (30).

5. The apparatus support (1) as claimed in claim 4, characterized in that the one or more damping elements (61, 62, 63, 64) are each formed by a rubber buffer (65).

6. The apparatus support (1) as claimed in claim 1, characterized in that the fastening device (40) has, on the upper face (31) of the mounting plate (30), a receiving contour (41) for receiving, with form-fit engagement, an underside of a medical apparatus that is to be received.

7. The apparatus support (1) as claimed in claim 1, characterized in that the fastening device (40) has, on the upper face (31) of the mounting plate (30), securing elements (43) by which a medical apparatus that is to be received is fixed with form-fit engagement.

8. The apparatus support (1) as claimed in claim 1, characterized in that the mounting plate (30) has a web structure (37) on the lower face (32), wherein hollows (38) are formed in the interspaces of the web structure (37).

9. The apparatus support (1) as claimed in claim 1, characterized in that it has an infusion stand (70) which, in the intended mounting state, is oriented exactly or at least substantially vertically.

10. A medical assembly having an apparatus holder (1) as claimed in claim 1 and having a mobile medical apparatus from the group comprising a defibrillator, an oxygen apparatus, a ventilator, a monitor, an infusion apparatus, an inhalation apparatus, an electrocardiograph, a transfusion pump, a life support system, an extracorporeal system, and a heart-lung machine (HLM), wherein the mobile medical apparatus has a housing underside or tubular frame, with which the mobile medical apparatus is arranged on the upper face of the mounting plate and is fastened with the fastening device.

* * * * *